United States Patent [19]

Fuller

[11] Patent Number: 4,898,185

[45] Date of Patent: Feb. 6, 1990

[54] BACK TRACTION DEVICE FOR USE WITH CHAIRS

[75] Inventor: Ernest Fuller, Walled Lake, Mich.

[73] Assignee: Life Support, Inc., Walled Lake, Mich.

[21] Appl. No.: 314,970

[22] Filed: Feb. 24, 1989

[51] Int. Cl.⁴ .............................................. A61F 13/00
[52] U.S. Cl. ............................. 128/876; 128/DIG. 15; 128/101.1; 128/898
[58] Field of Search ............... 128/874, 875, 876, 873, 128/870, 869, 846, DIG. 15, 101.1

[56] References Cited

U.S. PATENT DOCUMENTS

| | | | |
|---|---|---|---|
| 3,276,432 | 10/1966 | Murcott | 128/874 X |
| 4,022,197 | 5/1977 | Castiglia | 128/101.1 |
| 4,286,588 | 9/1981 | Lovegrove | 128/DIG. 15 |
| 4,487,201 | 12/1984 | Ciambarella et al. | 128/876 |

Primary Examiner—Robert A. Hafer
Assistant Examiner—Lynda M. Cofsky
Attorney, Agent, or Firm—Dykema Gossett

[57] ABSTRACT

A back traction device is disclosed that allows a patient or person to be seated in any type of seat and will relieve the pressure and tension on the disc of the lower back of the patient as much as possible. The back traction device comprises a halter with ribs that serve to transfer some of the pressure that is associated with setting in a chair when the patient is seated in the chair. The back traction device includes a halter and a traction member. The halter has strips of Velcro TM at an outward rear position that mate with Velcro TM portions on the traction device that is attached to a chair or the like. In one embodiment, the traction device comprises a member that has straps that allow it to be removably attached to a chair and, in a second embodiment, the Velcro TM traction device is permanently attached to the back of a chair. The second embodiment is particularly useful in a dedicated chair, for frequent use by people wearing such halter, such as a wheelchair.

11 Claims, 3 Drawing Sheets

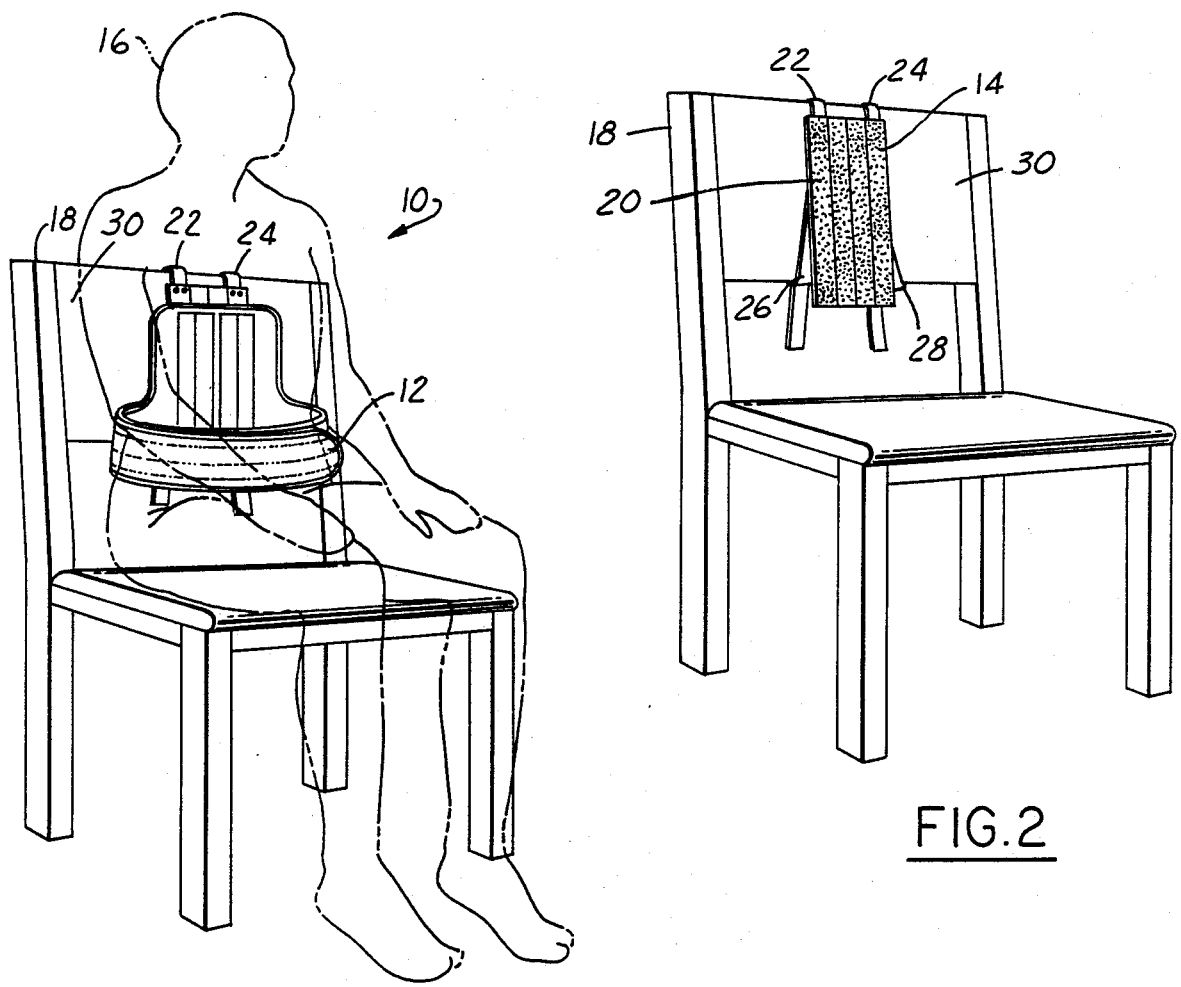
FIG.1
FIG.2
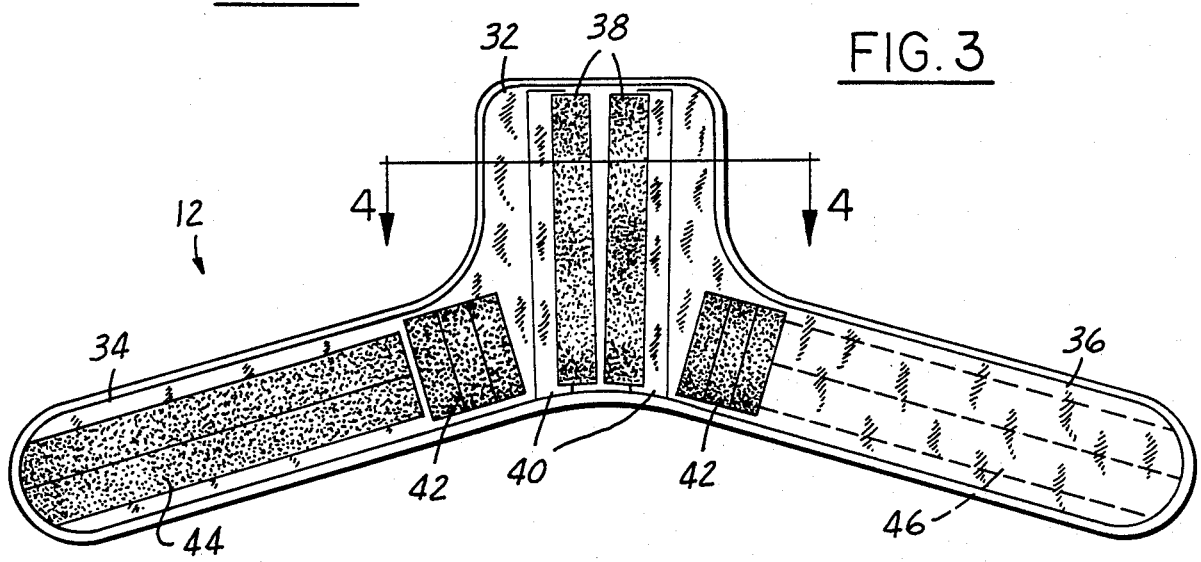
FIG.3

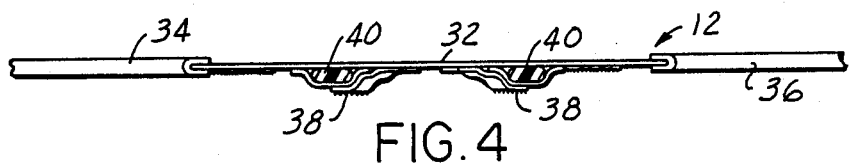
FIG. 4
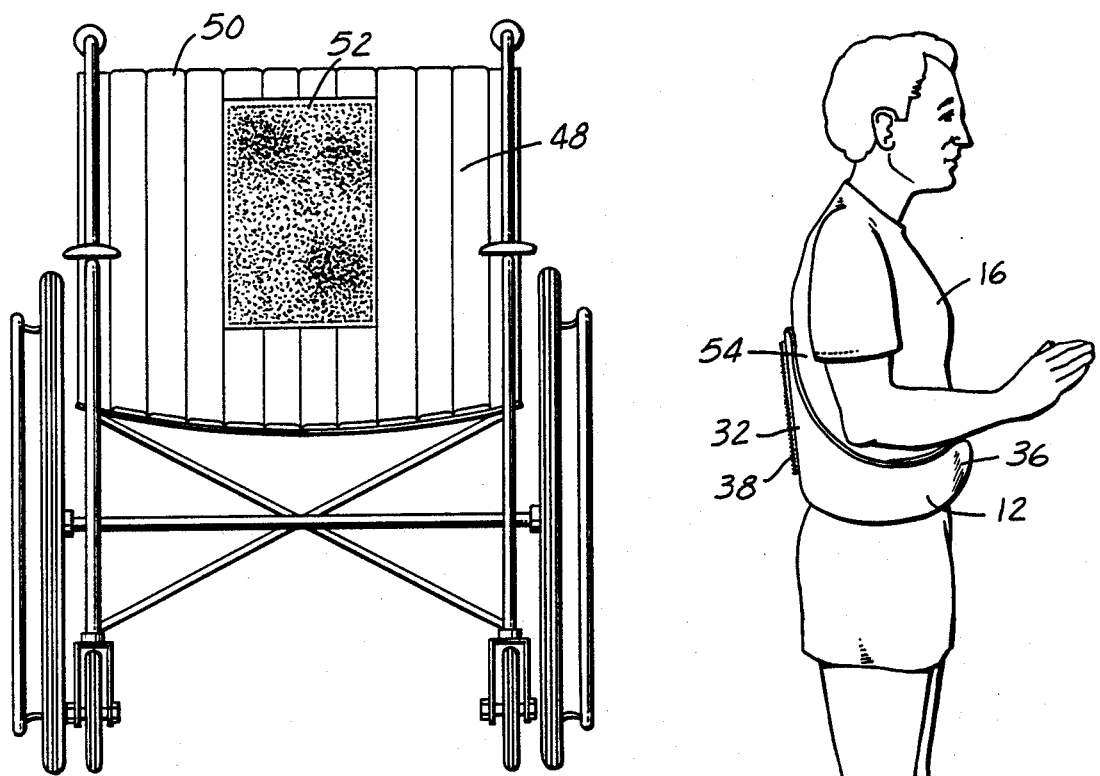
FIG. 5
FIG. 6
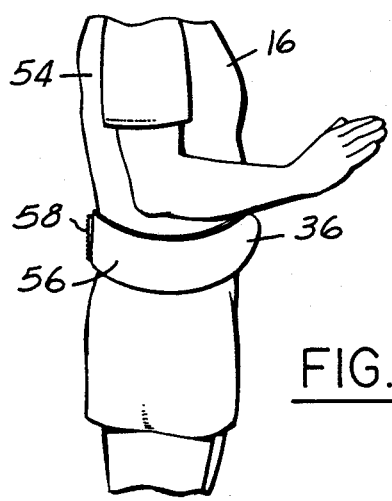
FIG. 7

BACK TRACTION DEVICE FOR USE WITH CHAIRS

BACKGROUND OF THE INVENTION

This invention in general relates to a back traction device and more particularly to such a a device including a halter member adapted to be worn by a person and a traction member adapted to be fitted to a chair. Such traction device, when the two members are adjustably secured together, with the patient or person seated in the chair, will provide traction to and reduce the pressure on the disc of the lower back. This results in a reduction of the pain in the lower back.

In the past several years, the medical literature has commented on various aspects regarding back injuries. Many of the authorities in the field suggest that a patient should not lay down for a long period of time after a severe back injury, but instead should begin resuming normal activities as soon as possible. Of course, these normal activities would include such things as sitting in a chair.

Other articles in the medical literature have studied the effect of various postures upon a patient's back. It has been determined that a seating position increases the pressure on a person's lower back by a factor of as much as 140% to 200% of body weight. It has been determined that it is important that a back injury patient have very good support and thereby decrease the pressure in the disc of the lower back as much as possible when using a seat of any type. The medical literature suggested the use of various types of seats with adjustable backs that will conform to and support a patient's back properly.

To actually achieve the above-stated goals has been difficult in practice since a patient might be exposed to several types of chairs in any one day. Even a better or properly fitted chair results in an increase in the pressure in the disc of the lower back as much as 140%. The patient may be utilizing an automobile chair, an airplane seat, or any type of office chair. It is impractical for all of these types of chairs to be adjustable to the individual's back.

Back braces are known that transfer some of the pressure from the disc to other structure in a patient's back. This type of thoracic halter is fitted around the patient to secure and stabilize him. However, such devices, while relieving tension or pressure from the disc of the lower back, do not solve the overall problem.

It would be desirable to transfer or decrease some of the pressure that is associated with sitting to allow the chair to carry the load when the patient is seated in the chair rather than the "other structure" in a patient's back.

It would also be desirable for the traction device to be used by a person with any type of chair having a seat in which the individual sits.

It is therefore an object of this invention to provide a back traction device that has a thoracic halter worn by a user and a traction member mounted on the back of a chair whereby, when the user is seated, the pressure in the disc of the lower back is transferred to the chair, relieving the patient's or user's lower back pain.

It is further an object of this invention to provide such a back traction device that may be adapted for use with any type of chair or any type of waist-worn halter construction.

Moreover, it is an object of the present invention to provide such a seated or back traction device including a combination halter member and traction member that is relatively simple to manufacture and utilize.

SUMMARY OF THE INVENTION

The invention consists of a combination of a traction member and a back halter member, wherein both the traction member and the back halter member have mating securing surfaces formed thereon. The halter member is fitted around the user or patient, the traction member is attached to a chair, and the patient or user then is seated in the chair. The mating securing surfaces on the traction member and the halter or halter member are engaged, and the weight of the upper body of the wearer is transferred from the halter to the chair through the back traction device.

The traction member of the back traction device may be fitted to any chair and can be adapted so as to be fitted over airline seats or the like. In addition, if a chair is to be dedicated, that is, used solely by an individual who will be wearing such a combination, the chair may have the mating surface formed integrally thereon. For instance, a wheelchair may have a mating securing portion formed on the back of the upholstery that will secure a halter that may be worn by the wheelchair occupant.

A preferred embodiment of the present invention consists of a halter or halter member that has an elongate central portion and two elongate wing portions that wrap around the patient's waist. The wing portions are formed with mating securing surfaces that secure the halter to the patient, and the elongate central portion is formed with a securing surface on the rear thereof. The securing surface on the rear of the elongate central portion of the halter is mounted preferably around the waist to support the ribs and upper body weight from the halter, thus better transferring the weight from the halter to the chair. The securing surfaces are preferably formed of a hook and loop fastening means or strips.

The traction device in a preferred embodiment consists of a sheet of hook and loop fastening material that will mate with the hook and loop fastening material means attached to the back of the halter and has straps that allow it to be attached to any type of seat or chair. The elongate straps that are attached to the rear of the traction member may be wrapped around the back of a chair or around the headrest of an automobile or airline seat.

These and other features and objects of the present invention can be best understood upon study of the attached specification and drawings, of which the following is a brief description thereof.

BRIEF DESCRIPTION OF THE DRAWINGS

FIG. 1 is a perspective view showing the combination of a halter and traction member attached to a chair with a seat occupant shown in phantom.

FIG. 2 shows the traction member of the present invention mounted to the back of a chair.

FIG. 3 is a plan view showing a thoracic halter as disclosed by the present invention.

FIG. 4 is a cross-section taken along lines 4—4 of FIG. 3.

FIG. 5 shows a wheelchair with a traction member as disclosed by the present invention.

FIG. 6 shows a patient wearing a thoracic halter as disclosed by the present invention.

FIG. 7 shows a patient wearing a second embodiment of the halter, also as disclosed by the present invention.

DETAILED DESCRIPTION OF A PREFERRED EMBODIMENT

Figure 8:
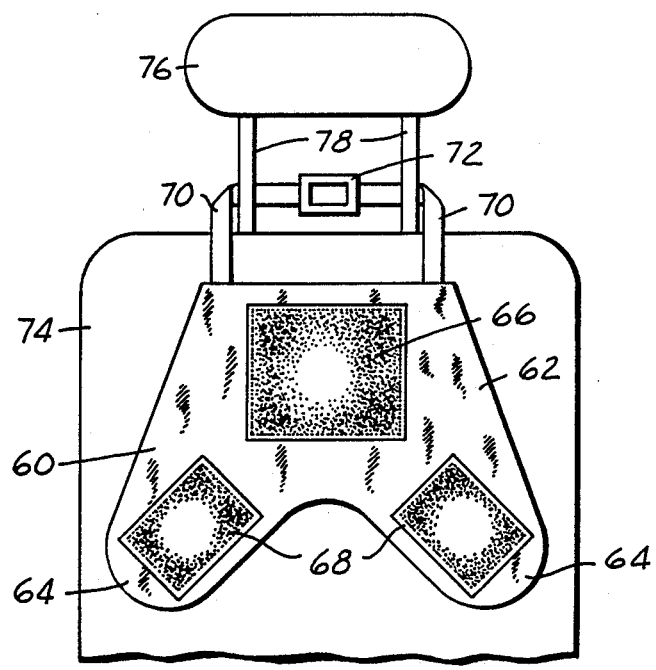
FIG. 8 shows a second embodiment of the traction member removably attached to an automobile seat.

The basic features of the present invention can be best understood upon a study of FIGS. 1–4 and 6. As shown in FIG. 1, the back traction device or assembly 10 consists of a thoracic halter 12 and an associated traction member or device 14. The halter is attached to a patient shown in phantom at 16, and the traction member 14 is removably attached to chair 18. It is to be understood that traction member 14 has a securing surface facing outwardly from chair 18, and halter 12 has a second securing surface formed facing outwardly away from the rear of patient or user 16 that mates with the securing surface on traction member 14.

As can be seen in FIG. 2, a prefered embodiment of traction member 14 consists of hook and loop fastening material securing surface 20 and two top tie members 22 and 24 that are associated with bottom tie members 26 and 28. In the preferred embodiment, the tie members all have mating hook and loop fastening material surfaces that are attached to each other on the rear of back 30 of chair 18. Since ties 22, 24, 26, 28 all have hook and loop fastening material attachments, the length of these ties may be adjusted to suit a particular chair back length. In addition, these ties would allow the traction member to be fitted around a headrest or other type of seat.

The details of thoracic halter 12 as disclosed by the present invention may be best understood from FIG. 3. As seen in FIG. 3, thoracic halter 12 consists of an elongate central portion 32 and two elongate wing portions 34 and 36. Elongate central portion 32 has two elongate hook and loop fastening material portions 38 extending along its entire length that overlie support ribs 40. Further hook and loop fastening material members 42 are disposed on each side of the support ribs 40. Wing 34 is formed with hook and loop fastening material portion 44, and wing 36 is formed with mating hook and loop fastening material portion 46 on the opposite side thereof.

As can best be seen from FIG. 6, this halter is fitted around the patient or user with wing 36 overlying wing 34 around the waist of the patient 16, and elongate central portion 32 extends upwardly along back 54 of patient 16.

As can be understood from these figures, the hook and loop fastening material strips 38 that are formed extending outwardly from the rear of halter 12 will align and be adjustably secured to hook and loop fastening material portion 20 on traction member 14. This transfers some of the pressure from the disc of the lower back through the halter 12 to traction member 14 to allow the chair to carry the load.

FIG. 4 shows a cross-section along lines 4—4 in FIG. 3 and shows the composition of halter 12. As can be seen from FIG. 4, the intermediate section or central portion 32 is formed of strengthened support ribs 40 that are partially overlaid by hook and loop fastening material portions 38. It is an important feature of this invention that the hook and loop fastening material portions 38 overlie support ribs 40, since this will aid in transferring the load from the halter 12 to the traction member 14 and therethrough to chair 18.

FIG. 5 shows an embodiment of the present invention in which a wheelchair 48 has a securing surface such as hook and loop fastening material portion 52 permanently attached to the rear 50 of the wheelchair seat. The present invention envisions a permanent attachment of the securing surface to the seat back whenever a seat is dedicated, that is, used exclusively by a wearer of this type of halter. Of course, this wheelchair could also have been fitted by a traction member or device similar to member 14 having the ties 22, 24, 26, 28.

FIG. 7 shows a patient 16 wearing a modified halter 56 that does not have the enlarged central section such as shown by the first embodiment of the halter. The halter 56 is more of a cummerbund shape but does include securing portion 58 that will again be secured to the traction member 14.

FIG. 8 illustrates a most preferred embodiment of the invention. As shown in FIG. 8, traction member 60 consists of an enlarged central portion 62 and two opposed wing portions 64. The enlarged central portion 62 has a securing portion 66 formed on a portion of the surface thereof. The two wing portions 64 each have a mating securing portion 68 formed on their surface area. The securing portions are preferably formed of hook and loop fastening material securing means or fasteners. Belts 70 extend from the top of central portion 62 and removably secure traction device or member 62 to an automobile seat, such as the automobile seat back 74. As illustrated in FIG. 8, straps 70 have been connected by a belt buckle 72 that allows the straps to be adjusted to securely hold traction member 60 to seat 74. Straps 70 are shown as attaching traction member 60 to head rest 76 by wrapping around the columns 78 of head rest 76.

Figure 9:
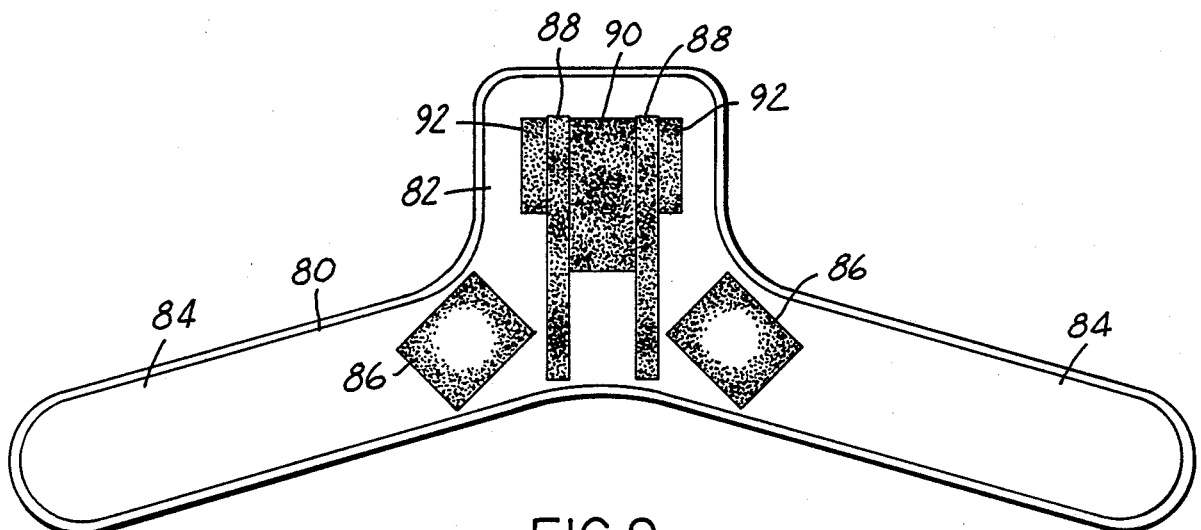
FIG. 9 is a plan view of a third embodiment of the thoracic halter as disclosed by the present invention.

FIG. 9 shows an improved thoracic halter 80 for use with traction member 60. Thoracic halter 80 has a central portion 82 and two opposed wing portions 84. The two opposed wing portions 84 each have hook and loop fastening material securing means, not illustrated, similar to hook and loop fastening material portions 44, 46 illustrated in FIG. 3. Securing portions 86 are formed on the rear surface of thoracic halter 80 at positions laterally spaced from central securing portions 88, 90, and 92. As illustrated, there are relatively long strips 88 and relatively shorter central and end strips 90 and 92. The strips 88 are of a first longitudinal extent being measured from the vertical when the patient is wearing halter 80. The longitudinal extent of securing portion 66, being measured from the vertical when the traction device 60 is mounted to a seat 74, is of a second longitudinal extent that is shorter than the first longitudinal extent. This difference in longitudinal extent between the securing portions on the halter 80 and traction member 60 allows halter 80 to be mounted at any one of several positions with respect to traction member 60. This allows the combination to be utilized by various sizes of patients or users.

Hook and loop fastening materials available under the Trademark Velcro TM, are representative of the hook and loop type fasteners which may be used as the securing surfaces in this invention.

Preferred embodiment of the present invention have been disclosed; however, certain modifications will be obvious to one of ordinary skill in the art. The intended scope of Applicant's invention can be best understood upon a reading of the appended claims.

I claim:

1. A method of relieving some of the pressure on the disc of the lower back of a person comprising the steps of:
   (A) securing a halter around the person's waist;
   (B) securing a traction device to a chair having a seat; and
   (C) adjustably attaching the halter to the traction device when the person is seated in the seat;
   (D) said halter being formed with hook and loop fastener portions at its rear and the traction device being formed with mating hook and loop fastener portions that secures the halter to the traction device, the use of the hook and loop fastener portions allowing the traction device and the halter to be adjustably attached at any one of a variety of positions.

2. A method as recited in claim 1, and further wherein said traction device is attached as part of the upholstery on the back of a wheelchair.

3. A method as recited in claim 1, and wherein said traction device has two straps that allow it to be secured to a chair, said two straps having a belt buckle associated therewith to allow them to be secured to a chair.

4. A method as recited in claim 1, and further wherein said traction device hook and loop fastener portions extending for a first distance measured along a longitudinal direction that will correspond to the vertical when the traction device is positioned on a chair, said halter hook annd loop fastener portions extending for a second distance measured along a longitudinal direction that will correspond to the vertical when the halter is positioned on a person, said second distance being greater than said first distance.

5. A method as recited in claim 4, and wherein the surface of said traction device hook and loop fastener portions has a first central portion and two opposed wing portions mounted laterally spaced from said central portion and said halter securing surface also has a first central portion and two opposed wing portions mounted laterally spaced from said central portion, said central portions of said halter and said traction device mating with each other when a person is seated, and said wing portions of said halter and said traction device also mating when a person is seated.

6. A method as recited in claim 5, and further wherein said halter has a pair of longitudinally extending support ribs, said central portion of said halter securing surface at least partially overlying said support ribs.

7. A method as recited in claim 6, and wherein said traction device has two straps that allow it to be secured to a chair, said two straps having a belt buckle associated therewith to allow them to be secured to a chair.

8. A method as recited in claim 1, and further wherein said chair is an airplane seat.

9. A method as recited in claim 1, and further wherein said chair is an automobile seat.

10. A method of relieving some of the pressure on the disc of the lower back of a person comprising the steps of:
    (A) securing a halter around the person's waist;
    (B) securing a traction device to the upholstery on a back of a wheelchair; and
    (C) attaching the halter to the traction device by attaching means while the person is seated in the wheelchair;
    (D) wherein said halter is formed with hook and loop fastener portions at its rear that overlie support ribs of the halter and the traction device is formed with mating hook and loop fastener portions that act as the securing means for securing the halter, the use of hook and loop fastener portions allowing the traction device and the halter to be adjustably attached at any one of a variety of positions.

11. A method of relieving some of the pressure on the disc of the lower back of a person comprising the steps of:
    (A) securing a halter around the person's waist;
    (B) securing a traction device to a chair or the like having a seat; and
    (C) attaching the halter to the traction device by attaching means while the person is seated in the seat;
    (D) wherein said halter is formed with hook and loop fastener portions at its rear that overlie support ribs of the halter and the traction device is formed with mating hook and loop fastener portions that act as the securing means for securing the halter, the use of hook and loop fastener portions allowing the traction device and the halter to be adjustably attached at any one of a variety of positions.

* * * * *